US012582601B2

(12) United States Patent
Agell Puig

(10) Patent No.: US 12,582,601 B2
(45) Date of Patent: Mar. 24, 2026

(54) ORODISPERSIBLE POWDER COMPOSITION

(71) Applicant: BIOPHARMA SYNERGIES, S.L., Barcelona (ES)

(72) Inventor: Francesc Agell Puig, Barcelona (ES)

(73) Assignee: BIOPHARMA SYNERGIES, S.L., Barcelona (ES)

( * ) Notice: Subject to any disclaimer, the term of this patent is extended or adjusted under 35 U.S.C. 154(b) by 339 days.

(21) Appl. No.: 18/255,675

(22) PCT Filed: Dec. 21, 2021

(86) PCT No.: PCT/IB2021/062096
§ 371 (c)(1),
(2) Date: Jun. 2, 2023

(87) PCT Pub. No.: WO2022/144691
PCT Pub. Date: Jul. 7, 2022

(65) Prior Publication Data
US 2024/0366502 A1 Nov. 7, 2024

(30) Foreign Application Priority Data
Dec. 30, 2020 (EP) ..................................... 20383177

(51) Int. Cl.
| | |
|---|---|
| *A61K 9/00* | (2006.01) |
| *A61K 9/14* | (2006.01) |
| *A61K 9/20* | (2006.01) |
| *A61K 45/06* | (2006.01) |

(52) U.S. Cl.
CPC ............ *A61K 9/0056* (2013.01); *A61K 9/145* (2013.01); *A61K 9/2018* (2013.01); *A61K 45/06* (2013.01)

(58) Field of Classification Search
CPC .... A61K 9/0056; A61K 9/145; A61K 9/2018; A61K 45/06
See application file for complete search history.

(56) References Cited

U.S. PATENT DOCUMENTS

| | | | |
|---|---|---|---|
| 10,434,150 B2 | 10/2019 | Berner et al. | |
| 2006/0024335 A1* | 2/2006 | Roger | A61K 9/0056 424/400 |

| | | | |
|---|---|---|---|
| 2006/0198885 A1 | 9/2006 | Dharmadhikari et al. | |
| 2009/0105265 A1* | 4/2009 | Kamali | A61P 43/00 514/249 |
| 2013/0203721 A1 | 8/2013 | Bhutada et al. | |

FOREIGN PATENT DOCUMENTS

| | | | | |
|---|---|---|---|---|
| WO | WO-2015144830 A1 * | 10/2015 | .............. | A61P 43/00 |
| WO | WO-2015200842 A1 * | 12/2015 | ........... | A61K 31/733 |

OTHER PUBLICATIONS

International Search Report issued on Apr. 4, 2022, in corresponding International Application No. PCT/IB2021/062096, 2 pages.
C. A. Challener, "Adapting APIs for Specially Dosage Forms", Pharmaceutical Technology Europe, Nov. 2019 2019, pp. 16-18, 3 pages.
Gala et al., "Taste Masking Techniques in the Pharmaceutical Industry", American Pharmaceutical Review, 2014, 17 (4) 1-6, 7 pages.
Savita et al., "Taste masking: a novel approach for better patient compliance", Journal of Pharamaceutical and Scientific Innovation, 2012, 1(3), 6-10, 5 pages.
AlAteibi et al., "Taste masking approaches for unpleasant taste drugs", Open Access Journal, vol. 2.1, 2019, 3 pages.
Coupland et al., "Physical Approaches to Masking Bitter Taste: Lessons from Food and Pharmaceuticals", Pharm. Res., 2014, 31(11), 2921-2939, 36 pages.
"Pharmaceutical Technology", Nov. 2019, vol. 43, No. 11, 60 pages.
D. Limmer et al., "Remington: The Science and Practice of Pharmacy", Lippincott Williams & Wilkins, 2000, 4 pages.
R.C. Rowe et al., "Handbook of Pharmaceutical Excipients", Pharmaceutical Press, sixth edition, 2009, 7 pages.
M.E. Aulton et al., "Aulton's Pharmaceutics The design and manufacture of medicines", Churchill Livingstone Elsevier, Fourth Edition, 2013, 5 pages.
F. Thomas, "Avoiding Bitter Taste", Pharmaceutical Technology Europe, 2019, 19-21, 3 pages.
R.C. Rowe et al., "Handbook of Pharmaceutical Excipients", Pharmaceutical Press, sixth edition, 2009, 917 pages.

* cited by examiner

*Primary Examiner* — Sean M Basquill
(74) *Attorney, Agent, or Firm* — Maier & Maier, PLLC

(57) ABSTRACT

An orodispersible powder composition including an active pharmaceutical ingredient and a ternary synergistic combination of sodium citrate, citric acid and sucralose. It also relates to a stick pack and a tablet including such orodispersible powder composition, and their use as a medicament.

14 Claims, No Drawings

ORODISPERSIBLE POWDER COMPOSITION

TECHNICAL FIELD

The present invention relates to pharmaceutical compositions comprising an active pharmaceutical ingredient, which are dosed in the form of stick packs as orodispersible powders.

BACKGROUND

The oral route is considered the most convenient and easy route for the administration of medicaments. In this case, a good taste is required to get patient compliance, as disclosed in C. A. Challener, Adapting APIs for Specially Dosage Forms, Pharm. Technol. Europe, 2019, 16-18, and in F. Thomas, Avoiding Bitter Taste, Pharm. Technol. Europe, 2019, 19-21.

However, active pharmaceutical ingredients are usually characterized by an unpleasant bitter taste, and as the solubility of the active ingredient in saliva increases, so does its offensive taste, as disclosed in US-A-2006/0198885.

In the state of the art, different approaches to mask the bitterness of active pharmaceutical ingredients have been proposed as disclosed in Gala et al., Taste Masking Techniques in the Pharmaceutical Industry, Am. Pharm. Rev., 2014, 17 (4) 1-6, and in Savita et al., Taste masking: a novel approach for better patient compliance, J. Pharm. Sci. Innnov., 2012, 1 (3), 6-10:

a) Addition of sweetener or flavouring agent
b) Complexation of the drug molecule into the cavity of a complexing agent.
c) Complexation with ion exchange resins
d) Coating of the pharmaceutical form, e.g., tablet
e) Microencapsulation of the active pharmaceutical ingredient.
f) Liposomes
g) Mass extrusion
h) Solid dispersion
i) Multiple emulsions
j) Entrapment of the drug into a bulky matrix of polymeric, resinous, gelling, or lipid materials.
k) Modification of bitter loci by prodrug formation.
l) Salt formation to retard the solubility of the active pharmaceutical ingredient in saliva.

Effervescent compositions releasing carbon dioxide have also been used to mask the bitter taste of drugs, as disclosed, for example in AlAteibi et al., Taste masking approaches for unpleasant taste drugs, Open Access J., 2019, DOI: 10.31021/ddddj.20191107

Pharmaceutical oral liquid compositions are used to mask the bitter taste of drugs. Water is a taste masking agent, since the degree of bitterness suppression depends on the concentration of active pharmaceutical ingredient in the saliva, as disclosed in Coupland et al., Physical Approaches to Masking Bitter Taste: Lessons from Food and Pharmaceuticals, Pharm. Res., 2014, 31 (11), 2921-2939.

Despite the various proposals available in the state of the art, there is still a need to have new oral pharmaceutical compositions, comprising an active pharmaceutical ingredient, having a masked taste and a high degree of acceptance by the patient.

SUMMARY

The object of the present invention is an orodispersible powder composition.

A stick pack comprising the orodispersible powder composition is also part of the invention.

A tablet comprising the orodispersible powder composition is also part of the invention.

The orodispersible powder composition for use as a medicament is also part of the invention.

DETAILED DESCRIPTION OF THE EMBODIMENTS

The object of the present invention is an orodispersible powder composition, which comprises:

a) a pharmacologically effective amount of an active pharmaceutical ingredient or a pharmaceutically acceptable salt thereof,
b) a ternary combination consisting of sodium citrate, citric acid and sucralose, and
c) one or more further excipients,
wherein the content of sodium citrate is comprised between 55 wt % and 85 wt %, preferably between 60 wt % and 80 wt %; the content of citric acid is comprised between 5 wt % and 30 wt %, preferably between 10 wt % and 25 wt %, and the content of sucralose is comprised between 5 wt % and 25 wt %, preferably between 8 wt % and 20 wt % over the total weight of the ternary composition,
wherein the content of the ternary combination is at least 8 wt % of the total orodispersible powder composition, and
wherein enzymes, steroids, triptans and anti-histaminic compounds are excluded as active pharmaceutical ingredient.

In an embodiment, the orodispersible powder composition is not granulated. In a preferred embodiment, the orodispersible powder composition is not granulated.

In an embodiment, the orodispersible powder composition is not effervescent. In a preferred embodiment, the orodispersible powder composition is not effervescent.

The authors of the present invention have developed an orodispersible powder by direct mixing with optimum flow properties, masking the bitter taste of active pharmaceutical ingredients, excluding enzymes, steroids, triptans and anti-histaminic compounds, and exhibiting an excellent acceptance of the formulation by the patient. The masking of the bitter taste has been surprisingly produced by a synergistic effect between citric acid, sodium citrate and sucralose. The orodispersible formulation dissolves rapidly in the oral cavity (less than 15 seconds), leaving no product residue in the mouth, and without the need to drink water after administration. Additionally, orodispersible powders of the invention show surprisingly optimal flow properties even after long periods of storage at room temperature.

The orodispersible powder of the invention allows improving the treatment compliance and reducing manufacturing costs. Further, the formulation is suitable for diabetics and for lactose intolerant.

In the context of the present invention, an orodispersible powder is a solid pharmaceutical composition, wherein the active pharmaceutical ingredient and the excipients are in powder form and which disperses and/or dissolves rapidly in the oral cavity. Rapidly means in less than 30 seconds, preferably in less than 20 seconds, and more preferably in less than 15 seconds.

In the context of the present invention, the term "pharmaceutical active compound" refers both to an active pharmaceutical ingredient and to a pharmaceutically acceptable salt thereof.

In the present description, as well as in the claims, the singular forms "a", "an" and "the" include the plural reference unless the context clearly indicates otherwise. The ranges defined by the preposition the terms "between . . . and . . . " or by the terms "from . . . to . . . " include also the two ends thereof. The term "about" refers to a deviation of plus/minus 10%, preferably plus/minus 5%. The percentages are expressed in % by weight (wt %), unless stated the contrary.

Active Pharmaceutical Compound

The active ingredient of the orodispersible powder of the present invention is an active pharmaceutical ingredient or a pharmaceutically acceptable salt thereof, excluding enzymes, steroids, triptans and anti-histaminic compounds.

As used herein, the term "pharmaceutically acceptable salt" refers to a salt prepared from pharmacologically acceptable anions, such as, for example, acetate, adipate, anthranilate, ascorbate, benzenesulfonate, benzoate, bisulfate, bitartrate, camphorsulfonate, ethanesulfonate, formate, fumarate, furoate, galacturonate, gentisate, gluconate, glucuronate, glutamate, glycolate, hydrobromide, hydrochloride, hydroiodide, isethionate, isonicotinate, lactate, malate, maleate, malonate, mandelate, mesylate, mucate, nitrate, pamoate, pantothenate, phentylacetate, phosphate, propionate, saccharate, salicylate, stearate, succinate, sulfanilate, sulfate, tartrate, p-toluenesulfonate, and hydrates thereof.

The active pharmaceutical ingredient is preferably selected from an agent for attention deficit hyperactivity disorder (ADHD) therapy, analgesic agent, anti-asthmatic agent, anti-bacterial agent, anti-dementia agent, anti-depressant agent, anti-diabetic agent, anti-emetic agent, anti-epileptic agent, anti-hypercholesterolemia agent, anti-hypertensive agent, anti-inflammatory agent, anti-psychotic agent, anti-retroviral agent, anti-thrombotic agent, anti-viral agent, anxiolytic agent, agent for erectile dysfunction therapy, gastrointestinal function conditioning agent, chemotherapeutic agent, anti-Parkinson's agent, agent for cystic fibrosis therapy, agent for benign prostatic hyperplasia, and mixtures thereof; more preferably selected from an agent for attention deficit hyperactivity disorder (ADHD) therapy, analgesic agent, anti-asthmatic agent, anti-bacterial agent, anti-dementia agent, anti-depressant agent, anti-diabetic agent, anti-emetic agent, anti-epileptic agent, anti-hypercholesterolemia agent, anti-hypertensive agent, anti-inflammatory agent, anti-psychotic agent, anti-retroviral agent, anti-thrombotic agent, anti-viral agent, anxiolytic agent, agent for erectile dysfunction therapy, gastrointestinal function conditioning agent, anti-Parkinson's agent, and mixtures thereof.

Active pharmaceutical ingredients belonging to the above mentioned therapeutic indications are, for example: atomoxetine and lisdexamphetamine as agents for attention deficit hyperactivity disorder (ADHD) therapy; tramadol as analgesic; montelukast as anti-asthmatic; amoxycillin as anti-bacterial; donepezil and memantine as anti-dementia agents; fluoxetine and mirtazapine as anti-depressant agents; dapagliflozin, metformin, sitagliptin, vildagliptin, and mixtures thereof as anti-diabetic agents; ondansetron as anti-emetic agent; pregabalin as anti-epileptic agent; atorvastatin, ezetimibe, simvastatin, and mixtures thereof as anti-hypercholesterolemia agents; amlodipine, olmesartan medoxomil, hydrochlorothiazide (HCTZ), valsartan, candesartan, indapamide, perindopril, sacubitril, and mixtures thereof as anti-hypertensive agents; etoricoxib as anti-inflammatory agent; carbidopa, levodopa, entacapone, and mixtures thereof as anti-Parkinson's agents; aripiprazol and olanzapine as anti-psychotic agents; abacavir, lamivudine, dolutegravir, cobicistat, darunavir, emtricitabine, tenofovir alafenamide, tenofovir disoproxil, elvitegravir, efavirenz, rilpivirine, and mixtures thereof as anti-retroviral agents; clopidogrel and rivaroxaban as anti-thrombotic agents; acyclovir, elbasvir, grazoprevir, glecaprevir, pibrentasvir, ledipasvir, sofosbuvir, velpatasvir, voxilaprevir, and mixtures thereof as anti-viral agents; alprazolam as anxiolytic agent; dutasteride, tamsulosin, and mixtures thereof as agents for benign prostatic hyperplasia; ivacaftor, lumacaftor, and mixtures thereof as agents for cystic fibrosis therapy; tadalafil as agent for erectile dysfunction therapy; and butylscopolamine, domperidone and loperamide as gastrointestinal function conditioning agents.

The active pharmaceutical ingredient is preferably selected from the group of atomoxetine, lisdexamphetamine, tramadol, montelukast, amoxycillin, donepezil, memantine, fluoxetine, mirtazapine, dapagliflozin, metformin, sitagliptin, vildagliptin, ondansetron, pregabalin, atorvastatin, ezetimibe, simvastatin, amlodipine, olmesartan medoxomil, hydrochlorothiazide, valsartan, candesartan, indapamide, perindopril, sacubitril, etoricoxib, carbidopa, levodopa, entacapone, aripiprazol, olanzapine, abacavir, lamivudine, dolutegravir, cobicistat, darunavir, emtricitabine, tenofovir alafenamide, tenofovir disoproxil, elvitegravir, efavirenz, rilpivirine, clopidogrel, rivaroxaban, acyclovir, elbasvir, grazoprevir, glecaprevir, pibrentasvir, ledipasvir, sofosbuvir, velpatasvir, voxilaprevir, alprazolam, dutasteride, tamsulosin, ivacaftor, lumacaftor, tadalafil, butylscopolamine, domperidone, loperamide, and mixtures thereof.

The active pharmaceutical ingredient is more preferably selected from the group of acyclovir, alprazolam, amoxycillin, aripiprazole, atomoxetine, butylscopolamine, carbidopa, clopidogrel, dapagliflozine, dolutegravir, domperidone, donepezil, entacapone, etoricoxib, ezetimibe, fluoxetine, ledipasvir, levodopa, lisdexamphetamine, loperamide, memantine, metformin, sitagliptin, mirtazapine, montelukast, olanzapine, olmesartan, amlodipine, hydrochlorothiazide, ondansetron, pregabalin, rivaroxaban, simvastatin, sofosbuvir, tadalafil, tramadol or a pharmaceutically acceptable salt thereof, and mixtures thereof.

Mixtures that are specially preferred are dapagliflozine/metformin, metformin/sitagliptin, metformin/vildagliptin, atorvastatin/ezetimibe, simvastatin/ezetimibe, amlodipine/olmesartan medoxomil, amlodipine/olmesartan medoxomil/hydrochlorothiazide, amlodipine/valsartan, amlodipine/valsartan/hydrochlorothiazide, candesartan/hydrochlorothiazide, indapamide/amlodipine/perindopril, olmesartan/amlodipine/hydrochlorothiazide, sacubitril/valsartan, carbidopa/levodopa/entacapone, abacavir/lamivudine, abacavir/lamivudine/dolutegravir, cobicistat/darunavir, cobicistat/darunavir/emtricitabine/tenofovir alafenamide, cobicistat/elvitegravir/emtricitabine/tenofovir alafenamide, emtricitabina/efavirenz/tenofovir disoproxil, emtricitabina/tenofovir alafenamide, emtricitabina/tenofovir disoproxil, tenofovir alafenamide/emtricitabine/rilpivirine, tenofovir disoproxil/emtricitabine/rilpivirine, elbasvir/grazoprevir, glecaprevir/pibrentasvir, ledipasvir/sofosbuvir, sofosbuvir/velpatasvir, sofosbuvir/velpatasvir/voxilaprevir, dutasteride/tamsulosin, and ivacaftor/lumacaftor.

Above-mentioned active pharmaceutical ingredients are either commercially available or prepared according to procedures disclosed in prior art documents, easily available to the skilled person in the art, which are cited for example in the monographies for each active ingredient included in the handbook Index Merck published by the Royal Society of Chemistry.

The pharmacologically effective amount of each active pharmaceutical ingredient is well-known by the skilled person in the art. It can be from 1 mg to 1000 mg.

The content of the active pharmaceutical ingredient in the orodispersible powder of the invention is usually comprised from 0.04 wt % to 30 wt %, over the total weight of the orodispersible powder composition. If a pharmaceutically acceptable salt of an active pharmaceutical ingredient is used in the formulation, then the amount is corrected accordingly.

Ternary Combination

The orodispersible powder of the invention comprises a synergistic ternary combination consisting of sodium citrate, citric acid and sucralose. Preferably a ternary combination of sodium citrate anhydrous, citric acid anhydrous and sucralose.

Sodium citrate, as either the dihydrate or anhydrous material, is used in pharmaceutical formulations. It is used primarily as a buffering agent to adjust the pH.

Citric acid as either the monohydrate or anhydrous material, is used in pharmaceutical formulations. It is used primarily as a buffering agent to adjust the pH.

In the composition of the invention, sodium citrate is preferably anhydrous and citric acid is preferably anhydrous.

Sucralose is used as a sweetening agent in pharmaceutical applications. It has a sweetening power approximately 300-1000 times that of sucrose and has no aftertaste. It has no nutritional value, is noncariogenic, does not promote dental caries, and produces no glycemic response.

In the ternary combination, the content of sodium citrate is comprised from 55 wt % to 85 wt %, preferably from 60 wt % to 80 wt %, and more preferably from 61 wt % to 78 wt % over the total weight of the ternary composition.

In the ternary combination, the content of citric acid is comprised from 5 wt % to 30 wt %, preferably from 10 wt % to 25 wt %, and more preferably from 12 wt % to 22 wt % over the total weight of the ternary composition.

In the ternary combination, the content of sucralose is comprised from 5 wt % to 25 wt %, preferably from 8 wt % to 20 wt %, and more preferably from 10 wt % to 18 wt % over the total weight of the ternary composition.

The amounts of sodium citrate, citric acid and sucralose in the ternary composition are combined to make 100%. If hydrated forms of sodium citrate and/or citric acid are used, the amounts are corrected accordingly.

Preferred embodiments of the ternary composition comprise from 55 wt % to 85 wt % of sodium citrate, from 5 wt % to 30 wt % of citric acid and from 5 wt % to 25 wt % by weight of sucralose, more preferably from 60 wt % to 80 wt % of sodium citrate, from 10 wt % to 25 wt % of citric acid and from 8 wt % to 20 wt % of sucralose, and more preferably from 61 wt % to 78 wt % of sodium citrate, from 12 wt % to 22 wt % of citric acid and from 10 wt % to 18 wt % of sucralose, wherein the amounts of sodium citrate, citric acid and sucralose in the ternary composition are combined to make 100%.

The content of the ternary combination in the orodispersible powder composition is at least 8 wt %, preferably not more than 47 wt %, over the total orodispersible powder composition. The content of the ternary combination in the orodispersible powder composition may be adjusted by the skilled person in the art by means of routine work.

Surprisingly, the ternary combination is able to mask the bitter taste of different active pharmaceutical ingredients, belonging to different therapeutic groups, along of a broad range of ratios between the active pharmaceutical ingredient and ternary combination comprised between 1:0.8 and 1:250, as shown in the examples.

Other Excipients

The orodispersible powder of the invention may comprise generally further excipients, such as diluents, lubricants, glidants, flavouring agents, sweetening agents, acidulants, alkalizing agents, buffering agents, antioxidants and mixtures thereof.

Suitable excipients for use in the preparation of the orodispersible powder of the invention are described, for example, in the book Handbook of pharmaceutical excipients, R. C. Rowe, P. J. Sheskey and M. E. Quinn, editors, Pharmaceutical Press, sixth edition, 2009.

Further excipients that are usually included in the orodispersible powder of the invention are selected from the group comprising diluents, lubricants, glidants, flavouring agents and mixtures thereof.

In a preferred embodiment, the orodispersible powder comprise one or more further excipients selected from diluents, lubricants, glidants, flavouring agents and mixtures thereof.

Suitable diluents may comprise, for example, mannitol, sorbitol, xylitol, isomalt, erythritol, cellulose powdered, microcrystalline cellulose, silified microcrystalline cellulose, starch, calcium phosphate, calcium lactate, calcium carbonate, magnesium carbonate, magnesium oxide and mixtures thereof; preferably the diluent is mannitol. In a preferred embodiment, the composition does not comprise lactose.

Mannitol is used in pharmaceutical formulations. It is primarily used as a diluent, where it is of particular value since it is not hygroscopic and may thus be used with moisture-sensitive active pharmaceutical ingredients. It is commonly used as an excipient in the manufacture of chewable tablet formulations because of its negative heat of solution, sweetness, and 'mouth feel', imparting a cooling sensation in the mouth. It is also used as a diluent in rapidly dispersing oral dosage forms. Given orally, mannitol is not absorbed significantly from the gastrointestinal tract, and it is suitable for diabetic patients. Mannitol does not undergo Maillard reactions. It has a low caloric content and it is noncariogenic.

Generally, the diluent is present in an amount from 40 wt % to 90 wt %, preferably from 45 wt % to 87 wt % over the total weight of the orodispersible powder composition.

The orodispersible powder may further comprise a lubricant, wherein the lubricant is usually selected from the group consisting of talc, sodium benzoate, sodium stearyl fumarate, sodium lauryl sulfate, calcium stearate, magnesium stearate, zinc stearate, glyceryl behenate, stearic acid, glyceryl monostearate, poloxamer, polyethylene glycol and mixtures thereof; preferably the lubricant is sodium stearyl fumarate.

Sodium stearyl fumarate is used as a lubricant in pharmaceutical compositions. It is supplied in a pure form and is of value when the less pure stearate-type lubricants are unsuitable owing to chemical incompatibility. Sodium stearyl fumarate is less hydrophobic than magnesium stearate or stearic acid and has a less retardant effect on dissolution than magnesium stearate. Generally, the lubricant is present in an amount from 0.05 wt % to 10 wt %, preferably from 0.1 wt % to 5 wt %, more preferably from 0.2 wt % to 2.5 wt %, more preferably from 0.4 wt % to 1 wt %, more preferably from 0.45 wt % to 0.75 wt %, and yet more preferably about 0.5 wt % over the total weight of the orodispersible powder composition.

The orodispersible powder may further comprise a glidant, wherein the glidant is usually selected from the group consisting of colloidal silicon dioxide, calcium phosphate tribasic, hydrophobic colloidal silica, magnesium silicate, magnesium trisilicate, silicon dioxide, talc and mixtures thereof. The preferred glidant is colloidal silicon dioxide.

Colloidal silicon dioxide is used in pharmaceutical formulations. Its small particle size and large specific surface area give it desirable flow characteristics that are exploited to improve the flow properties of dry powders. Generally, the glidant is present in an amount from 0.05 wt % to 10 wt %, preferably from 0.1 wt % to 5 wt %, more preferably from 0.2 wt % to 2.5 wt %, more preferably from 0.4 wt % to 1 wt %, more preferably from 0.45 wt % to 0.75 wt %, and yet more preferably about 0.5 wt % over the total weight of the orodispersible powder composition.

The orodispersible powder may further comprise a flavouring agent, wherein it is usually selected from fruit flavours such as orange, banana, strawberry, cherry, wild cherry, lemon and mixtures thereof, and other flavours such as cardamom, anise, peppermint, menthol, vanillin and ethyl vanillin and mixtures thereof. preferably the flavouring agent comprises peppermint flavour. Generally, the content of the flavouring agent is comprised from 0.05 wt % to 5.0 wt % over the total weight of the orodispersible powder composition.

In some embodiments, the orodispersible powder may comprise a sweetening agent, which is usually selected from the group consisting of saccharin sodium, neohesperidin dihydrochalcone, acesulfame potassium, aspartame and mixtures thereof. Preferably the composition does not include sucrose, and therefore it is suitable for diabetics. Generally, the sweetening agent is usually present in an amount from 0.1 wt % to 5 wt % over the total weight of the orodispersible powder composition.

In some embodiments, the orodispersible powder may comprise an acidulant, which is usually selected from the group consisting of fumaric acid, maleic acid, malic acid, tartaric acid and mixtures thereof. Generally, the content of the acidulant is comprised from 0.1 wt % to 2.0 wt % over the total weight of the orodispersible powder composition.

In some embodiments, the orodispersible powder may comprise an alkalizing agent, which is usually selected from the group consisting of potassium bicarbonate, potassium citrate, sodium bicarbonate, sodium carbonate and mixtures thereof. Generally, the alkalizing agent is usually present in an amount from 1 wt % to 40 wt % over the total weight of the orodispersible powder composition.

In some embodiments, the orodispersible powder may comprise a buffering agent, which is usually selected from the group consisting of dibasic sodium phosphate, glycine, methionine and mixtures thereof. Generally, the content of the buffering agent is comprised from 1 wt % to 40 wt % over the total weight of the orodispersible powder composition.

In some embodiments, the orodispersible powder may comprise an antioxidant, which is usually selected from the group consisting of ascorbic acid, erythorbic acid, sodium ascorbate and mixtures thereof. Generally, the antioxidant is usually present in an amount from 0.1 wt % to 5 wt % over the total weight of the orodispersible powder composition.

Manufacturing Process

The process for preparing the orodispersible powder is a direct mixing of the components, which makes very attractive for industrial manufacturing. The process comprises generally sieving of the components through a 0.5 mm-1 mm mesh sieve, and mixing in, for example, a V-shaped mixer, which is suitable for free-flowing powders. Mixing time is adjusted according to routine practice to obtain a homogeneous mixture, which is dosed in stick packs.

Conventional mixing procedures, well-known to the skilled in pharmaceutical technology, are disclosed in reference books in the field, for example, in the book *Aulton's Pharmaceutics. The design and manufacture of medicines*, M. E. Aulton and K. M. G. Taylor, editors, Churchill Livingstone Elsevier, Fourth Edition, 2013; or in the book *Remington: The Science and Practice of Pharmacy*, D. Limmer editor, Lippincott Williams & Wilkins, 2000.

Stick Pack

A stick pack comprising the orodispersible powder of the invention also forms part of the invention.

A stick pack is a packaging form, usually having a laminate structure to give a specific barrier and sealing characteristics. It is used for a single dose administration. It is of common use containing pharmaceutical compositions or foods, e.g., sugar. Materials usually employed to manufacture stick packs are aluminium, paper, polyethylene, polyethylene terephthalate, propylene and combinations thereof.

The stick pack comprises a dose of a pharmacologically effective amount of the orodispersible powder composition, which comprises an active pharmaceutical ingredient.

The stick pack usually comprises an amount of the orodispersible powder composition, which is comprised between 1 g and 10 g, preferably between 1.5 g and 5 g, and more preferably between 1.9 g and 3.5 g.

The new orodispersible powder formulation obtained by direct mixing of the components provides an excellent masking of the bitter taste of the active pharmaceutical ingredient with an excellent acceptance of the formulation by the patient.

Orodispersible powders that are obtained by direct mixing of active pharmaceutical ingredient, and stick packs comprising the orodispersible powder composition obtained by direct mixing, are not commercially available.

Direct mixing of the components allows the direct exposure of the active pharmaceutical ingredient in the oral cavity, increasing the dissolution rate of the active pharmaceutical ingredient and its absorption in the oral cavity, favouring the fast effect of the medication, which is considered a very important attribute and valued by both patients and doctors.

In this invention the stick pack packaging form has been chosen because it is practical, robust, easy to transport and use individually, so it adapts well to a modern and active lifestyle. The patient can carry the stick pack always on top and it can be taken without the need to drink water, increasing the effectiveness of the active pharmaceutical ingredient.

The orodispersible powder composition of the invention has industrial application, since a direct mixing process is used as manufacturing process, which is widely used in the pharmaceutical industry, and, in addition, as shown in the examples, the formulation exhibits optimal rheological characteristics according to the European Pharmacopoeia current edition, and, therefore, it can be scale up at industrial level, so that it can be dosed on equipment with the stick pack packaging format.

As shown in the examples, the orodispersible powder composition of the invention shows a high degree of acceptance by the patient for active pharmaceutical ingredients over a broad range of compositions.

In an embodiment, the orodispersible powder composition can be compressed into a tablet. Thus, a tablet comprising the orodispersible powder composition is also part of the invention.

Use

The orodispersible powder composition, the stick pack and the tablet of the invention for use as a medicament also form part of the invention.

In a preferred embodiment, the orodispersible powder composition, the stick pack and the tablet of the invention are for use as a medicament.

The present invention comprises the following embodiments:

1.—An orodispersible powder composition, characterized in that it comprises:
   a) a pharmacologically effective amount of an active pharmaceutical ingredient or a pharmaceutically acceptable salt thereof,
   b) a ternary combination consisting of sodium citrate, citric acid and sucralose, and
   c) one or more further excipients,
   wherein the content of sodium citrate is comprised between 55 wt % and 85 wt %, preferably between 60 wt % and 80 wt %, and more preferably from 61 wt % to 78 wt %; the content of citric acid is comprised between 5 wt % and 30 wt %, preferably between 10 wt % and 25 wt %, and more preferably from 12 wt % to 22 wt %; and the content of sucralose is comprised between 5 wt % and 25 wt %, preferably between 8 wt % and 20 wt %, and more preferably from 10 wt % to 18 wt % over the total weight of the ternary composition,
   wherein the content of the ternary combination is at least 8 wt % of the total orodispersible powder composition, and
   wherein enzymes, steroids, triptans and anti-histaminic compounds are excluded as active pharmaceutical ingredient.

2.—The orodispersible powder composition according to embodiment 1, characterized in that the active pharmaceutical ingredient is selected from an agent for attention deficit hyperactivity disorder (ADHD) therapy, analgesic agent, anti-asthmatic agent, antibacterial agent, anti-dementia agent, anti-depressant agent, anti-diabetic agent, anti-emetic agent, anti-epileptic agent, anti-hypercholesterolemia agent, anti-hypertensive agent, anti-inflammatory agent, anti-psychotic agent, anti-retroviral agent, anti-thrombotic agent, anti-viral agent, anxiolytic agent, agent for erectile dysfunction therapy, gastrointestinal function conditioning agent, chemotherapeutic agent, anti-Parkinson's agent, agent for cystic fibrosis therapy, agent for benign prostatic hyperplasia, and mixtures thereof; preferably selected from an agent for attention deficit hyperactivity disorder (ADHD) therapy, analgesic agent, anti-asthmatic agent, anti-bacterial agent, anti-dementia agent, anti-depressant agent, anti-diabetic agent, anti-emetic agent, anti-epileptic agent, anti-hypercholesterolemia agent, anti-hypertensive agent, anti-inflammatory agent, anti-psychotic agent, anti-retroviral agent, anti-thrombotic agent, anti-viral agent, anxiolytic agent, agent for erectile dysfunction therapy, gastrointestinal function conditioning agent, anti-Parkinson's agent, and mixtures thereof.

3.—The orodispersible powder composition according to embodiment 2, characterized in that the active pharmaceutical ingredient is selected from atomoxetine and lisdexamphetamine as agents for attention deficit hyperactivity disorder (ADHD) therapy; tramadol as analgesic; montelukast as anti-asthmatic; amoxycillin as anti-bacterial; donepezil and memantine as anti-dementia agents; fluoxetine and mirtazapine as anti-depressant agents; dapagliflozin, metformin, sitagliptin, vildagliptin, and mixtures thereof as anti-diabetic agents; ondansetron as anti-emetic agent; pregabalin as anti-epileptic agent; atorvastatin, ezetimibe, simvastatin, and mixtures thereof as anti-hypercholesterolemia agents; amlodipine, olmesartan medoxomil, hydrochlorothiazide (HCTZ), valsartan, candesartan, indapamide, perindopril, sacubitril, and mixtures thereof as anti-hypertensive agents; etoricoxib as anti-inflammatory agent; carbidopa, levodopa, entacapone, and mixtures thereof as anti-Parkinson's agents; aripiprazol and olanzapine as anti-psychotic agents; abacavir, lamivudine, dolutegravir, cobicistat, darunavir, emtricitabine, tenofovir alafenamide, tenofovir disoproxil, elvitegravir, efavirenz, rilpivirine, and mixtures thereof as anti-retroviral agents; clopidogrel and rivaroxaban as anti-thrombotic agents; acyclovir, elbasvir, grazoprevir, glecaprevir, pibrentasvir, ledipasvir, sofosbuvir, velpatasvir, voxilaprevir, and mixtures thereof as anti-viral agents; alprazolam as anxiolytic agent; dutasteride, tamsulosin, and mixtures thereof as agents for benign prostatic hyperplasia; ivacaftor, lumacaftor, and mixtures thereof as agents for cystic fibrosis therapy; tadalafil as agent for erectile dysfunction therapy; and butylscopolamine, domperidone and loperamide as gastrointestinal function conditioning agents.

4.—The orodispersible powder composition according to embodiment 3, characterized in that the active pharmaceutical ingredient is selected from atomoxetine, lisdexamphetamine, tramadol, montelukast, amoxycillin, donepezil, memantine, fluoxetine, mirtazapine, dapagliflozin, metformin, sitagliptin, vildagliptin, ondansetron, pregabalin, atorvastatin, ezetimibe, simvastatin, amlodipine, olmesartan medoxomil, hydrochlorothiazide, valsartan, candesartan, indapamide, perindopril, sacubitril, etoricoxib, carbidopa, c levodopa, entacapone, aripiprazol, olanzapine, abacavir, lamivudine, dolutegravir, cobicistat, darunavir, emtricitabine, tenofovir alafenamide, tenofovir disoproxil, elvitegravir, efavirenz, rilpivirine, clopidogrel, rivaroxaban, acyclovir, elbasvir, grazoprevir, glecaprevir, pibrentasvir, ledipasvir, sofosbuvir, velpatasvir, voxilaprevir, alprazolam, dutasteride, tamsulosin, ivacaftor, lumacaftor, tadalafil, butylscopolamine, domperidone, loperamide, and mixtures thereof.

5.—The orodispersible powder composition according to embodiment 4, characterized in that the active pharmaceutical ingredient is selected from acyclovir, alprazolam, amoxycillin, aripiprazole, atomoxetine, butylscopolamine, carbidopa, clopidogrel, dapagliflozine, dolutegravir, domperidone, donepezil, entacapone, etoricoxib, ezetimibe, fluoxetine, ledipasvir, levodopa, lisdexamphetamine, loperamide, memantine, metformin, sitagliptin, mirtazapine, montelukast, olanzapine, olmesartan, amlodipine, hydrochlorothiazide, ondansetron, pregabalin, rivaroxaban, simvastatin, sofosbuvir, tadalafil, tramadol or a pharmaceutically acceptable salt thereof, and mixtures thereof.

6.—The orodispersible powder composition according to embodiment 4, characterized in that the active pharmaceutical ingredient is a mixture selected from dapagliflozine/metformin, metformin/sitagliptin, metformin/vildagliptin, atorvastatin/ezetimibe, simvastatin/ezetimibe, amlodipine/olmesartan medoxomil, amlodipine/olmesartan medoxomil/hydrochlorothiazide, amlodipine/valsartan, amlodipine/valsartan/ hydrochlorothiazide, candesartan/hydrochlorothiazide, indapamide/amlodipine/perindopril, olmesartan/amlodipine/hydrochlorothiazide, sacubitril/valsartan, carbidopa/levodopa/entacapone, abacavir/lamivudine, abacavir/lamivudina/dolutegravir, cobicistat/darunavir, cobicistat/darunavir/emtricitabine/tenofovir alafenamide, cobicistat/elvitegravir/emtricitabine/tenofovir alafenamide, emtricitabina/efavirenz/tenofovir disoproxil, emtricitabina/tenofovir alafenamide, emtricitabina/tenofovir disoproxil, tenofovir alafenamide/ emtricitabine/rilpivirine, tenofovir disoproxil/ emtricitabine/rilpivirine, elbasvir/grazoprevir, glecaprevir/pibrentasvir, ledipasvir/sofosbuvir, sofosbuvir/velpatasvir, sofosbuvir/velpatasvir/voxilaprevir, dutasteride/tamsulosin, and ivacaftor/lumacaftor.

7.—The orodispersible powder composition according to any of embodiments 1 to 6, characterized in that the ternary composition comprises from 55 wt % to 85 wt % of sodium citrate, from 5 wt % to 30 wt % of citric acid and from 5 wt % to 25 wt % by weight of sucralose; preferably from 60 wt % to 80 wt % of sodium citrate, from 10 wt % to 25 wt % of citric acid and from 8 wt % to 20 wt % of sucralose, and more preferably from 61 wt % to 78 wt % of sodium citrate, from 12 wt % to 22 wt % of citric acid and from 10 wt % to 18 wt % of sucralose, wherein the amounts of sodium citrate, citric acid and sucralose in the ternary composition are combined to make 100%.

8.—The orodispersible powder composition according to any of embodiments 1 to 7, characterized in that the content of the ternary composition is not more than 47 wt %, over the total orodispersible powder composition.

9.—The orodispersible powder composition according to any one of embodiments 1 to 8, characterized in that sodium citrate is anhydrous and citric acid is anhydrous.

10.—The orodispersible powder composition according to any one of embodiments 1 to 9, characterized in that one or more further excipients are selected from diluents, lubricants, glidants, flavouring agents, sweetening agents, acidulants, alkalizing agents, buffering agents, antioxidants and mixtures thereof.

11.—The orodispersible powder composition according to embodiment 10, characterized in that the diluent is selected from mannitol, sorbitol, xylitol, isomalt, erythritol, cellulose powdered, microcrystalline cellulose, silified microcrystalline cellulose, starch, calcium phosphate, calcium lactate, calcium carbonate, magnesium carbonate, magnesium oxide and mixtures thereof.

12.—The orodispersible powder composition according to embodiment 11, characterized in that the diluent is mannitol.

13.—The orodispersible powder composition according to embodiment 11 or 12, characterized in that the diluent is present in an amount from 40 wt % to 90 wt %, preferably from 45 wt % to 87 wt % over the total weight of the orodispersible powder composition.

14.—The orodispersible powder composition according to embodiment 10, characterized in that the lubricant is selected from the group consisting of talc, sodium benzoate, sodium stearyl fumarate, sodium lauryl sulfate, calcium stearate, magnesium stearate, zinc stearate, glyceryl behenate, stearic acid, glyceryl monostearate, poloxamer, polyethylene glycol and mixtures thereof.

15.—The orodispersible powder composition according to embodiment 14, characterized in that the lubricant is sodium stearyl fumarate.

16.—The orodispersible powder composition according to embodiment 14 or 15, characterized in that the lubricant is present in an amount from 0.05% to 10%, preferably from 0.1% to 5%, more preferably from 0.2% to 2.5%, more preferably from 0.4% to 1%, more preferably from 0.45% to 0.75%, and yet more preferably about 0.5% by weight over the total weight of the orodispersible powder composition.

17.—The orodispersible powder composition according to embodiment 10, characterized in that the glidant is selected from the group consisting of colloidal silicon dioxide, calcium phosphate tribasic, hydrophobic colloidal silica, magnesium silicate, magnesium trisilicate, silicon dioxide, talc and mixtures thereof.

18.—The orodispersible powder composition according to embodiment 17, characterized in that the glidant is colloidal silicon dioxide.

19.—The orodispersible powder composition according to embodiment 17 or 18, characterized in that the glidant is present in an amount from 0.05% to 10%, preferably from 0.1% to 5%, more preferably from 0.2% to 2.5%, more preferably from 0.4% to 1%, more preferably from 0.45% to 0.75%, and yet more preferably about 0.5% by weight over the total weight of the orodispersible powder composition.

20.—The orodispersible powder composition according to embodiment 10, characterized in that the flavouring agent is selected from orange, banana, strawberry, cherry, wild cherry, lemon, cardamom, anise, peppermint, menthol, vanillin and ethyl vanillin and mixtures thereof.

21.—The orodispersible powder composition according to embodiment 20, characterized in that the flavouring agent comprises peppermint flavour.

22.—The orodispersible powder composition according to embodiment 20 or 21, characterized in that the content of the flavouring agent is comprised from 0.05% to 5.0% by weight over the total weight of the orodispersible powder composition.

23.—A stick pack comprising the orodispersible powder composition according to any one of embodiments 1 to 22.

24.—The stick pack according to embodiment 23, characterized in that it comprises a dose of a pharmacologically effective amount of the orodispersible powder composition, which comprises an active pharmaceutical ingredient.

25.—The stick pack according to embodiment 23 or 24, characterized in that it comprises an amount of the orodispersible powder composition, which is comprised between 1 g and 10 g, preferably between 1.5 g and 5 g, and more preferably between 1.9 g and 3.5 g.

26.—A tablet comprising the orodispersible powder composition according to any one of embodiments 1 to 22.

27.—The orodispersible powder composition according to any one of embodiments 1 to 22 and the stick pack of any one of embodiments 23 to 25 and the tablet of embodiment 26 for use as a medicament.

In the following examples, different embodiments of the invention are provided for illustrative purposes that are understood to be non-limiting.

EXAMPLES

According to the European Pharmacopeia 10th edition, monograph 2.9.36. Powder flow, the physical properties of pharmaceutical powders are of upmost importance in the pharmaceutical industry. The powders flow behaviour is a key factor in a series of unit processes such as blending, filling, transportation and in scale-up operations.

In the drug development stage, an accurate assessment of the flow properties is essential in order to identify the optimum formulation. To evaluate the powder flow properties, parameters such as, angle of repose, compressibility index and the Hausner ratio, are generally employed. These methods are recommended by the pharmacopeia's to evaluate powders flowability, they are easy to handle and their application is widely used in industrial applications and in scale-up operations.

Angle of Repose

The angle of repose has been used in several branches of science to characterize the flow properties of solids. Angle of repose is a characteristic related to interparticulate friction or resistance to movement between particles.

The angle of repose is the constant, three-dimensional angle measured relatively to the horizontal base, assumed by a cone-like pile of material formed when the powder is passed through a funnel-like container.

An angle of repose lower than 40°, indicates good flowability, conversely an angle of repose superior to 40° is an indication of cohesiveness.

Compressibility Index and Hausner Ratio

The compressibility index and the Hausner ratio are used as an indirect measure of bulk density, size and shape, surface area, moisture content, and cohesiveness of materials because all of these can influence the compressibility index and the Hausner ratio.

The compressibility index and the Hausner ratio are calculated taking into account the unsettled apparent volume and the final tapped volume of the powder, after tapping the material until no further volume changes occur.

The compressibility index measures the tendency of the powder to consolidate. This parameter has an inverse relation with flowability, i.e., the more compressible is the material the less flowable it will be. A powder with a compressibility index lower than 20% is considered to have a good flowability.

The Hausner ratio is a useful measure of cohesion reflecting particle friction. With a Hausner ratio higher than 1.40, the powder is considered a cohesive difficult to fluidize powder. Ratios lower than 1.25 characterizes a free-flowing powder.

Statistical Analysis

Statistical analysis of the data obtained was carried out using paired t-test with the help of Minitab software. Paired t-test is a statistical test that compares the means of two groups of observations on the same or related subject over time or in differing circumstances.

Examples 1-72: Orodispersible Powders

Orodispersible powders comprising different active pharmaceutical ingredients were prepared according to a process comprising the following steps:

1) Sieving all the components through a 0.5 mm mesh sieve (except the citric acid anhydrous that is sieved through a 1 mm mesh sieve), and incorporate them into the V-shaped mixer in the following order: sodium citrate anhydrous, sucralose, flavouring agent, active ingredient, colloidal silicon dioxide, mannitol, citric acid anhydrous, and any optional excipient.
2) Mixing about 15 minutes at about 20 rpm in the V-mixer.
3) Sieving the sodium stearyl fumarate through a 0.5 mm mesh sieve and incorporate it into the V-mixer.
4) Mix about 5 minutes at about 20 rpm in the V-mixer.
5) Dosing the product in stick packs (for example, 2200-3500 mg per stick).

Examples 1-36 were prepared using anhydrous forms of citric acid and sodium citrate, whereas examples 37-72 were prepared combining anhydrous and hydrated forms of citric acid and sodium citrate, while maintaining the active pharmaceutical ingredient and the rest of components.

Orodispersible powders according to the invention were prepared for different active pharmaceutical ingredients (API) as shown in Table I, which further includes the ratio by weight API: ternary combination and content of the ternary combination in the orodispersible powder composition:

TABLE I

| Example | API | ratio 1:x | wt % ternary combination |
|---|---|---|---|
| 1/37 | rivaroxaban | 25 | 11.4 |
| 2/38 | pregabalin | 3.33 | 11.4 |
| 3/39 | sitagliptin phosphate monohydrate | 17 | 34 |
| 4/40 | clopidogrel bisulphate | 15.5 | 46.6 |
| 5/41 | olmesartan medoxomil | 31.5 | 28.6 |
| 6/42 | tadalafil | 25 | 11.4 |
| 7/43 | carbidopa | 25.2 | 28.6 |
| 8/44 | dolutegravir sodium | 17 | 34 |
| 9/45 | simvastatin | 31.5 | 28.6 |
| 10/46 | amoxicillin trihydrate | 1 | 16.7 |
| 11/47 | acyclovir | 1.25 | 8.3 |
| 12/48 | etoricoxib | 28.3 | 38.7 |
| 13/49 | olmesartan (20 mg)/ amlodipine 5 mg)/ HCTZ (12.5 mg) | 16.8 | 28.6 |
| 14/50 | metformin (1000 mg)/ sitagliptin (50 mg) | 0.81 | 24.28 |
| 15/51 | ezetimibe | 63 | 28.6 |
| 16/52 | dapagliflozine | 63 | 28.6 |
| 17/53 | atomoxetine | 15.75 | 28.6 |
| 18/54 | montelukast | 25 | 11.4 |
| 19/55 | donepezil | 25 | 11.4 |
| 20/56 | loperamide | 125 | 11.4 |
| 21/57 | ondansetron | 62.5 | 11.4 |
| 22/58 | deflazacort | 41.7 | 11.4 |
| 23/59 | tramadol | 12.6 | 28.6 |
| 24/60 | memantine | 31.5 | 28.6 |
| 25/61 | butylscopolamine bromide | 25 | 11.4 |
| 26/62 | alprazolam | 250 | 11.4 |
| 27/63 | fluoxetine | 31.5 | 28.6 |
| 28/64 | lisdexamphetamine | 21 | 28.6 |
| 29/65 | olanzapine | 50 | 11.4 |
| 30/66 | domperidone | 63 | 28.6 |
| 31/67 | mirtazapine | 42 | 28.6 |
| 32/68 | aripiprazol | 63 | 28.6 |
| 33/69 | sofosbuvir | 2.1 | 24.28 |
| 34/70 | entacapone | 3.15 | 28.6 |
| 35/71 | levodopa | 12.6 | 28.6 |
| 36/72 | ledipasvir | 9.44 | 24.28 |

Tables II-X show quantitative compositions of orodispersible powders. The content is expressed in mg and wt %, wherein the absence of decimal means exact value:

TABLE II

| Component | Example 1 | | Example 2 | | Example 3 | | Example 4 | |
|---|---|---|---|---|---|---|---|---|
| | mg | wt % | mg | wt % | mg | wt % | mg | wt % |
| API | 10 | 0.45 | 75 | 3.40 | 64.2 | 2.57 | 97.9 | 3.92 |
| Flavour | 5 | 0.23 | 5 | 0.23 | 5 | 0.2 | 5 | 0.20 |
| Sodium citrate anhydrous | 154 | 7.0 | 154 | 7.0 | 600 | 24 | 900 | 36 |
| Citric acid anhydrous | 54.3 | 2.5 | 54.3 | 2.47 | 130 | 5.2 | 140 | 5.6 |
| Sucralose | 41.8 | 1.9 | 41.8 | 1.9 | 120 | 4.8 | 125 | 5 |
| Mannitol | 1913 | 86.92 | 1848 | 84 | 1558.8 | 62.35 | 1210.1 | 48.4 |
| Sodium stearyl fumarate | 11 | 0.5 | 11 | 0.5 | 11 | 0.44 | 11 | 0.44 |
| Colloidal silicon dioxide | 11 | 0.5 | 11 | 0.5 | 11 | 0.44 | 11 | 0.44 |
| Total | 2200 | 100 | 2200 | 100 | 2500 | 100 | 2500 | 100 |

TABLE III

| Component | Example 5 | | Example 6 | | Example 7 | | Example 8 | |
|---|---|---|---|---|---|---|---|---|
| | mg | wt % | mg | wt % | mg | wt % | mg | wt % |
| API | 25 | 1.14 | 10 | 0.45 | 25 | 1.14 | 52.6 | 2.1 |
| Flavour | 5 | 0.23 | 5 | 0.23 | 5 | 0.23 | 5 | 0.2 |
| Sodium citrate anhydrous | 400 | 18.2 | 154 | 7.0 | 400 | 18.2 | 600 | 24 |
| Citric acid anhydrous | 130 | 5.9 | 54.3 | 2.5 | 130 | 5.9 | 130 | 5.2 |
| Sucralose | 100 | 4.53 | 41.8 | 1.9 | 100 | 4.53 | 120 | 4.8 |
| Mannitol | 1518 | 69 | 1913 | 86.92 | 1518 | 69 | 1570.4 | 62.82 |
| Sodium stearyl fumarate | 11 | 0.5 | 11 | 0.5 | 11 | 0.5 | 11 | 0.44 |
| Colloidal silicon dioxide | 11 | 0.5 | 11 | 0.5 | 11 | 0.5 | 11 | 0.44 |
| Total | 2200 | 100 | 2200 | 100 | 2200 | 100 | 2500 | 100 |

TABLE IV

| Component | Example 9 | | Example 10 | | Example 11 | | Example 12 | |
|---|---|---|---|---|---|---|---|---|
| | mg | wt % | mg | wt % | mg | wt % | mg | wt % |
| API | 20 | 0.91 | 574 | 19.1 | 200 | 6.67 | 30 | 1.36 |
| Flavour | 5 | 0.23 | 5 | 0.2 | 5 | 0.17 | 5 | 0.23 |
| Sodium citrate anhydrous | 400 | 18.2 | 308 | 10.3 | 154 | 5.12 | 600 | 27.3 |
| Citric acid anhydrous | 130 | 5.9 | 108.6 | 3.6 | 54.3 | 1.81 | 130 | 5.91 |
| Sucralose | 100 | 4.53 | 83.6 | 2.8 | 41.8 | 1.39 | 120 | 5.5 |
| Mannitol | 1523 | 69.23 | 1898.8 | 63.2 | 2523 | 84.1 | 1293 | 58.7 |
| Sodium stearyl fumarate | 11 | 0.5 | 11 | 0.4 | 11 | 0.37 | 11 | 0.5 |
| Colloidal silicon dioxide | 11 | 0.5 | 11 | 0.4 | 11 | 0.37 | 11 | 0.5 |
| Total | 2200 | 100 | 3000 | 100 | 3000 | 100 | 2200 | 100 |

TABLE V

| Component | Example 13 mg | Example 13 wt % | Example 14 mg | Example 14 wt % | Example 15 mg | Example 15 wt % | Example 16 mg | Example 16 wt % |
|---|---|---|---|---|---|---|---|---|
| API | 37.5 | 1.7 | 1050 | 30 | 10 | 0.45 | 10 | 0.45 |
| Flavour | 5 | 0.23 | 5 | 0.14 | 5 | 0.23 | 5 | 0.23 |
| Sodium citrate anhydrous | 400 | 18.2 | 600 | 17.14 | 400 | 18.2 | 400 | 18.2 |
| Citric acid anhydrous | 130 | 5.9 | 130 | 3.72 | 130 | 5.9 | 130 | 5.9 |
| Sucralose | 100 | 4.54 | 120 | 3.43 | 100 | 4.54 | 100 | 4.54 |
| Mannitol | 1505.5 | 68.43 | 1573 | 44.95 | 1533 | 69.68 | 1533 | 69.68 |
| Sodium stearyl fumarate | 11 | 0.5 | 11 | 0.31 | 11 | 0.5 | 11 | 0.5 |
| Colloidal silicon dioxide | 11 | 0.5 | 11 | 0.31 | 11 | 0.5 | 11 | 0.5 |
| Total | 2200 | 100 | 3500 | 100 | 2200 | 100 | 2200 | 100 |

TABLE VI

| Component | Example 17 mg | Example 17 wt % | Example 18 mg | Example 18 wt % | Example 19 mg | Example 19 wt % | Example 20 mg | Example 20 wt % |
|---|---|---|---|---|---|---|---|---|
| API | 40 | 1.82 | 10 | 0.45 | 10 | 0.45 | 2 | 0.09 |
| Flavour | 5 | 0.23 | 5 | 0.23 | 5 | 0.23 | 5 | 0.23 |
| Sodium citrate anhydrous | 400 | 18.2 | 154 | 7.0 | 154 | 7.0 | 154 | 7.0 |
| Citric acid anhydrous | 130 | 5.9 | 54.3 | 2.5 | 54.3 | 2.5 | 54.3 | 2.5 |
| Sucralose | 100 | 4.54 | 41.8 | 1.9 | 41.8 | 1.9 | 41.8 | 1.9 |
| Mannitol | 1503 | 68.31 | 1913 | 86.92 | 1913 | 86.92 | 1921 | 87.28 |
| Sodium stearyl fumarate | 11 | 0.5 | 11 | 0.5 | 11 | 0.5 | 11 | 0.5 |
| Colloidal silicon dioxide | 11 | 0.5 | 11 | 0.5 | 11 | 0.5 | 11 | 0.5 |
| Total | 2200 | 100 | 2200 | 100 | 2200 | 100 | 2200 | 100 |

TABLE VII

| Component | Example 21 mg | Example 21 wt % | Example 22 mg | Example 22 wt % | Example 23 mg | Example 23 wt % | Example 24 mg | Example 24 wt % |
|---|---|---|---|---|---|---|---|---|
| API | 4 | 0.18 | 6 | 0.27 | 50 | 2.27 | 20 | 0.91 |
| Flavour | 5 | 0.23 | 5 | 0.23 | 5 | 0.23 | 5 | 0.23 |
| Sodium citrate anhydrous | 154 | 7.0 | 154 | 7.0 | 400 | 18.2 | 400 | 18.2 |
| Citric acid anhydrous | 54.3 | 2.47 | 54.3 | 2.47 | 130 | 5.9 | 130 | 5.9 |
| Sucralose | 41.8 | 1.9 | 41.8 | 1.9 | 100 | 4.54 | 100 | 4.54 |
| Mannitol | 1919 | 87.22 | 1917 | 87.13 | 1493 | 67.86 | 1523 | 69.22 |
| Sodium stearyl fumarate | 11 | 0.5 | 11 | 0.5 | 11 | 0.5 | 11 | 0.5 |
| Colloidal silicon dioxide | 11 | 0.5 | 11 | 0.5 | 11 | 0.5 | 11 | 0.5 |
| Total | 2200 | 100 | 2200 | 100 | 2200 | 100 | 2200 | 100 |

TABLE VIII

| Component | Example 25 | | Example 26 | | Example 27 | | Example 28 | |
|---|---|---|---|---|---|---|---|---|
| | mg | wt % | mg | wt % | mg | wt % | mg | wt % |
| API | 10 | 0.45 | 1 | 0.045 | 20 | 0.91 | 30 | 1.36 |
| Flavour | 5 | 0.23 | 5 | 0.23 | 5 | 0.23 | 5 | 0.23 |
| Sodium citrate anhydrous | 154 | 7.0 | 154 | 7.0 | 400 | 18.2 | 400 | 18.2 |
| Citric acid anhydrous | 54.3 | 2.47 | 54.3 | 2.47 | 130 | 5.9 | 130 | 5.9 |
| Sucralose | 41.8 | 1.9 | 41.8 | 1.9 | 100 | 4.54 | 100 | 4.54 |
| Mannitol | 1913 | 86.95 | 1922 | 87.355 | 1523 | 69.22 | 1513 | 68.77 |
| Sodium stearyl fumarate | 11 | 0.5 | 11 | 0.5 | 11 | 0.5 | 11 | 0.5 |
| Colloidal silicon dioxide | 11 | 0.5 | 11 | 0.5 | 11 | 0.5 | 11 | 0.5 |
| Total | 2200 | 100 | 2200 | 100 | 2200 | 100 | 2200 | 100 |

TABLE IX

| Component | Example 29 | | Example 30 | | Example 31 | | Example 32 | |
|---|---|---|---|---|---|---|---|---|
| | mg | wt % | mg | wt % | mg | wt % | mg | wt % |
| API | 5 | 0.23 | 10 | 0.45 | 15 | 0.68 | 10 | 0.45 |
| Flavour | 5 | 0.23 | 5 | 0.23 | 5 | 0.23 | 5 | 0.23 |
| Sodium citrate anhydrous | 154 | 7.0 | 400 | 18.2 | 400 | 18.2 | 400 | 18.2 |
| Citric acid anhydrous | 54.3 | 2.47 | 130 | 5.9 | 130 | 5.9 | 130 | 5.9 |
| Sucralose | 41.8 | 1.9 | 100 | 4.54 | 100 | 4.54 | 100 | 4.54 |
| Mannitol | 1918 | 87.17 | 1533 | 69.68 | 1528 | 69.45 | 1533 | 69.68 |
| Sodium stearyl fumarate | 11 | 0.5 | 11 | 0.5 | 11 | 0.5 | 11 | 0.5 |
| Colloidal silicon dioxide | 11 | 0.5 | 11 | 0.5 | 11 | 0.5 | 11 | 0.5 |
| Total | 2200 | 100 | 2200 | 100 | 2200 | 100 | 2200 | 100 |

TABLE X

| Component | Example 33 | | Example 34 | | Example 35 | | Example 36 | |
|---|---|---|---|---|---|---|---|---|
| | mg | wt % | mg | wt % | mg | wt % | mg | wt % |
| API | 400 | 11.43 | 200 | 9.09 | 50 | 2.27 | 90 | 2.57 |
| Flavour | 5 | 0.14 | 5 | 0.23 | 5 | 0.23 | 5 | 0.14 |
| Sodium citrate anhydrous | 600 | 17.14 | 400 | 18.2 | 400 | 18.2 | 600 | 17.14 |
| Citric acid anhydrous | 130 | 3.71 | 130 | 5.9 | 130 | 5.9 | 130 | 3.71 |
| Sucralose | 120 | 3.43 | 100 | 4.54 | 100 | 4.54 | 120 | 3.43 |
| Mannitol | 2223 | 63.51 | 1343 | 61.04 | 1493 | 67.86 | 2533 | 72.37 |
| Sodium stearyl fumarate | 11 | 0.32 | 11 | 0.5 | 11 | 0.5 | 11 | 0.32 |
| Colloidal silicon dioxide | 11 | 0.32 | 11 | 0.5 | 11 | 0.5 | 11 | 0.32 |
| Total | 3500 | 100 | 2200 | 100 | 2200 | 100 | 3500 | 100 |

It was confirmed that powders disperse and/or dissolve rapidly in the oral cavity, leaving no product residue in the mouth.

In the Examples 37-72, at least one of the anhydrous forms of citric acid and sodium citrate present in Examples 1-36 was substituted by the corresponding hydrated form, as shown in Table XI, maintaining unmodified the rest of the composition. The APIs present in the Examples 37-72 are shown in Table I, and correspond to the APIs present in the Examples 1-36, e.g., rivaroxaban is present both in Example 1 and in Example 37, pregabalin is present both in Example 2 and in Example 38, and so on. 10

TABLE XI

| Example | Reference Example | Components |
|---|---|---|
| 37 | 1 | Sodium citrate |
| 38 | 2 | dihydrate |
| 39 | 3 | Citric acid |
| 40 | 4 | anhydrous |
| 41 | 5 | |
| 42 | 6 | |
| 43 | 7 | |
| 44 | 8 | |
| 45 | 9 | |
| 46 | 10 | |
| 47 | 11 | |
| 48 | 12 | |
| 49 | 13 | Sodium citrate |
| 50 | 14 | anhydrous |
| 51 | 15 | Citric acid |
| 52 | 16 | monohydrate |
| 53 | 17 | |
| 54 | 18 | |
| 55 | 19 | |
| 56 | 20 | |
| 57 | 21 | |
| 58 | 22 | |
| 59 | 23 | |
| 60 | 24 | |
| 61 | 25 | Sodium citrate |
| 62 | 26 | dihydrate |
| 63 | 27 | Citric acid |
| 64 | 28 | monohydrate |
| 65 | 29 | |
| 66 | 30 | |
| 67 | 31 | |
| 68 | 32 | |
| 69 | 33 | |
| 70 | 34 | |
| 71 | 35 | |
| 72 | 36 | |

It was confirmed that powders disperse and/or dissolve rapidly in the oral cavity, leaving no product residue in the mouth.

Comparative Examples 73-108: Orodispersible Powders without the Ternary Synergistic Combination Comparative orodispersible powders 73-108 were prepared using the process disclosed for Examples 1-72, comprising the same API, and the rest of components, with the exception that they don't comprise the ternary synergistic combination. Taking into account that Comparative Examples did not include said ternary synergistic combination, only 36 compositions were prepared one for each pharmaceutical active ingredient, which were compared with the compositions comprising either anhydrous citric acid and anhydrous sodium citrate, or a combination of anhydrous and hydrated forms of citric acid and sodium citrate.

Each of said comparative orodispersible powders were organoleptically compared with the corresponding orodispersible powder of Examples 1-72 according to the invention, e.g., Example 1 vs Comparative Example 73, Example 2 vs Comparative Example 74, Example 36 vs Comparative Example 108, Example 37 vs Comparative Example 73, Example 38 vs Comparative Example 74, Example 72 vs Comparative Example 108, and so on.

Example 109: Testing of Orodispersible Powders Comprising Pharmaceutical Active Compounds a) Organoleptic Testing Organoleptic tests of the orodispersible powder formulations dosed in stick packs, were carried out in 6 healthy volunteers, which is according to the standard found in prior art publications, such as, for example, Noorjahan et al., In vivo evaluation of taste masking for developed chewable and orodispersible tablets in humans and rats, Pharma. Dev. Technol., 2014, 19 (3), 290-295.

The methodology for evaluating the acceptance of the formulations by the patient has consisted in establishing a score from 1 to 5 for the taste of the formulation (acid, sweet or salty), where 1 corresponds to an unacceptable taste, and 5 corresponds to an excellent taste, and another score from 1 to 5 to assess the bitterness of the formulation, wherein 1 corresponds to an unacceptable bitterness, and 5 corresponds to an excellent capacity for masking the bitterness of the active ingredient. The multiplication of the taste value of the formulation by the value referring to the capacity of masking the bitterness of the active ingredient, gives rise to a value that is the degree of acceptance of the formulation by the patient.

Table XII shows the results:

The results obtained indicate that the formulations masked the bitter taste of the pharmaceutical active compounds, with an excellent acceptance of the formulation by the patient, and without the need to drink water after the administration of the orodispersible formulation.

Moreover, t-student statistical test, applied to the results from the examples according to the invention and from the comparative examples, yielded values for $t_{experimental}$ clearly over the $t_{tabulated}$ ($\alpha=0.05$), as shown in Table XII, confirming that the presence of the ternary synergistic combination is the formulation factor that allows masking the bitter taste of a large variety of pharmaceutical active ingredients, which are present in a pharmaceutical dosage form, such as an orodispersible powder composition.

Results also show that there are not statistical differences associated to the form of citric acid and sodium citrate, i.e., anhydrous and hydrated forms, regarding the capacity of masking the bitter taste of the pharmaceutical active ingredients.

TABLE XII

| Ex. | Average (n = 6) | Std. dev. | Comp. Ex. | Average (n = 6) | Std. dev. | t exp ($\alpha = 0.05$) | t tab ($\alpha = 0.05$) |
|---|---|---|---|---|---|---|---|
| 1 | 25.0 | 0.0 | 73 | 5.3 | 1.8 | 24.5 | 1.8 |
| 2 | 25.0 | 0.0 | 74 | 4.0 | 2.0 | 23.5 | 1.8 |
| 3 | 20.2 | 2.6 | 75 | 1.0 | 0.0 | 16.4 | 1.8 |
| 4 | 20.8 | 1.9 | 76 | 1.0 | 0.0 | 23.8 | 1.8 |
| 5 | 25.0 | 0.0 | 77 | 6.7 | 1.8 | 22.8 | 1.8 |
| 6 | 25.0 | 0.0 | 78 | 3.2 | 1.2 | 40.2 | 1.8 |
| 7 | 25.0 | 0.0 | 79 | 7.0 | 1.4 | 28.5 | 1.8 |
| 8 | 25.0 | 0.0 | 80 | 2.2 | 0.9 | 56.9 | 1.8 |
| 9 | 25.0 | 0.0 | 81 | 6.0 | 2.2 | 19.0 | 1.8 |

TABLE XII-continued

| Ex. | Average (n = 6) | Std. dev. | Comp. Ex. | Average (n = 6) | Std. dev. | t exp (α = 0.05) | t tab (α = 0.05) |
|---|---|---|---|---|---|---|---|
| 10 | 25.0 | 0.0 | 82 | 2.2 | 1.3 | 38.0 | 1.8 |
| 11 | 25.0 | 0.0 | 83 | 2.7 | 0.9 | 53.0 | 1.8 |
| 12 | 19.5 | 3.0 | 84 | 1.0 | 0.0 | 13.4 | 1.8 |
| 13 | 23.3 | 2.4 | 85 | 4.3 | 1.4 | 15.6 | 1.8 |
| 14 | 19.3 | 1.5 | 86 | 1.0 | 0.0 | 27.5 | 1.8 |
| 15 | 25.0 | 0.0 | 87 | 6.7 | 1.8 | 22.8 | 1.8 |
| 16 | 25.0 | 0.0 | 88 | 5.8 | 1.7 | 25.6 | 1.8 |
| 17 | 21.2 | 4.1 | 89 | 1.0 | 0.0 | 11.1 | 1.8 |
| 18 | 25.0 | 0.0 | 90 | 7.0 | 1.4 | 28.5 | 1.8 |
| 19 | 25.0 | 0.0 | 91 | 6.3 | 2.1 | 20.3 | 1.8 |
| 20 | 25.0 | 0.0 | 92 | 6.7 | 1.8 | 22.8 | 1.8 |
| 21 | 25.0 | 0.0 | 93 | 8.5 | 1.1 | 33.0 | 1.8 |
| 22 | 23.3 | 2.4 | 94 | 2.2 | 0.4 | 19.8 | 1.8 |
| 23 | 25.0 | 0.0 | 95 | 4.8 | 1.7 | 26.9 | 1.8 |
| 24 | 25.0 | 0.0 | 96 | 8.0 | 1.4 | 26.9 | 1.8 |
| 25 | 22.5 | 2.5 | 97 | 1.8 | 0.4 | 18.3 | 1.8 |
| 26 | 25.0 | 0.0 | 98 | 7.5 | 1.5 | 26.1 | 1.8 |
| 27 | 21.7 | 2.4 | 99 | 2.8 | 0.9 | 16.7 | 1.8 |
| 28 | 20.8 | 1.9 | 100 | 2.3 | 1.2 | 18.4 | 1.8 |
| 29 | 25.0 | 0.0 | 101 | 6.2 | 1.5 | 28.8 | 1.8 |
| 30 | 23.3 | 2.4 | 102 | 7.5 | 1.5 | 12.7 | 1.8 |
| 31 | 25.0 | 0.0 | 103 | 5.7 | 0.7 | 58.0 | 1.8 |
| 32 | 25.0 | 0.0 | 104 | 8.5 | 1.1 | 33.0 | 1.8 |
| 33 | 20.2 | 2.6 | 105 | 1.0 | 0.0 | 16.4 | 1.8 |
| 34 | 23.3 | 2.4 | 106 | 3.3 | 1.5 | 16.0 | 1.8 |
| 35 | 24.2 | 1.9 | 107 | 5.7 | 0.7 | 20.6 | 1.8 |
| 36 | 25.0 | 0.0 | 108 | 2.7 | 0.9 | 53.0 | 1.8 |
| 37 | 25.0 | 0.0 | 73 | 5.3 | 1.8 | 24.5 | 1.8 |
| 38 | 25.0 | 0.0 | 74 | 4.0 | 2.0 | 23.5 | 1.8 |
| 39 | 20.2 | 2.6 | 75 | 1.0 | 0.0 | 16.4 | 1.8 |
| 40 | 19.3 | 1.5 | 76 | 1.0 | 0.0 | 27.5 | 1.8 |
| 41 | 25.0 | 0.0 | 77 | 6.7 | 1.8 | 22.8 | 1.8 |
| 42 | 24.2 | 1.9 | 78 | 3.2 | 1.2 | 21.1 | 1.8 |
| 43 | 25.0 | 0.0 | 79 | 7.0 | 1.4 | 28.5 | 1.8 |
| 44 | 25.0 | 0.0 | 80 | 2.2 | 0.9 | 56.9 | 1.8 |
| 45 | 24.2 | 1.9 | 81 | 6.0 | 2.2 | 14.0 | 1.8 |
| 46 | 25.0 | 0.0 | 82 | 2.2 | 1.3 | 38.0 | 1.8 |
| 47 | 24.2 | 1.9 | 83 | 2.7 | 0.9 | 23.0 | 1.8 |
| 48 | 19.5 | 3.0 | 84 | 1.0 | 0.0 | 13.4 | 1.8 |
| 49 | 23.3 | 2.4 | 85 | 4.3 | 1.4 | 15.6 | 1.8 |
| 50 | 19.3 | 1.5 | 86 | 1.0 | 0.0 | 27.5 | 1.8 |
| 51 | 23.3 | 2.4 | 87 | 6.7 | 1.8 | 12.6 | 1.8 |
| 52 | 25.0 | 0.0 | 88 | 5.8 | 1.7 | 25.6 | 1.8 |
| 53 | 21.2 | 4.1 | 89 | 1.0 | 0.0 | 11.1 | 1.8 |
| 54 | 23.3 | 2.4 | 90 | 7.0 | 1.4 | 13.3 | 1.8 |
| 55 | 25.0 | 0.0 | 91 | 6.3 | 2.1 | 20.3 | 1.8 |
| 56 | 25.0 | 0.0 | 92 | 6.7 | 1.8 | 22.8 | 1.8 |
| 57 | 25.0 | 0.0 | 93 | 8.5 | 1.1 | 33.0 | 1.8 |
| 58 | 22.7 | 3.5 | 94 | 2.2 | 0.4 | 13.0 | 1.8 |
| 59 | 25.0 | 0.0 | 95 | 4.8 | 1.7 | 26.9 | 1.8 |
| 60 | 23.3 | 2.4 | 96 | 8.0 | 1.4 | 12.5 | 1.8 |
| 61 | 22.5 | 2.5 | 97 | 1.8 | 0.4 | 18.3 | 1.8 |
| 62 | 25.0 | 0.0 | 98 | 7.5 | 1.5 | 26.1 | 1.8 |
| 63 | 21.7 | 2.4 | 99 | 2.8 | 0.9 | 16.7 | 1.8 |
| 64 | 20.8 | 1.9 | 100 | 2.3 | 1.2 | 18.4 | 1.8 |
| 65 | 23.3 | 2.4 | 101 | 6.2 | 1.5 | 13.8 | 1.8 |
| 66 | 23.3 | 2.4 | 102 | 7.5 | 1.5 | 12.7 | 1.8 |
| 67 | 25.0 | 0.0 | 103 | 5.7 | 0.7 | 58.0 | 1.8 |
| 68 | 25.0 | 0.0 | 104 | 8.5 | 1.1 | 33.0 | 1.8 |
| 69 | 20.2 | 2.6 | 105 | 1.0 | 0.0 | 16.4 | 1.8 |
| 70 | 23.3 | 2.4 | 106 | 3.3 | 1.5 | 16.0 | 1.8 |
| 71 | 24.2 | 1.9 | 107 | 5.7 | 0.7 | 20.6 | 1.8 |
| 72 | 24.2 | 1.9 | 108 | 2.7 | 0.9 | 23.0 | 1.8 | b) Physical Parameters

The following galenic parameters were determined in order to assess the flowability of the formulations: angle of repose (degrees), compressibility index (%) and Hausner ratio. The methodology of the European Pharmacopoeia 10th edition was used, as shown in Table XIII:

TABLE XIII

| Compressibility index | Hausner ratio | Angle of repose | Assessment |
|---|---|---|---|
| 1-10 | 1.00-1.11 | 25-30 | Excellent |
| 11-15 | 1.12-1.18 | 31-35 | Good |
| 16-20 | 1.19-1.25 | 36-40 | Fair |
| 21-25 | 1.26-1.34 | 41-45 | Passable |
| 26-31 | 1.35-1.45 | 46-55 | Poor |
| 32-37 | 1.46-1.59 | 56-65 | Very poor |
| >38 | >1.60 | >66 | Very, very poor |

Table XIV shows the results for orodispersible powders according to the invention:

TABLE XIV

| Example | Compressibility index | Hausner ratio | Angle of repose |
|---|---|---|---|
| 1 | 9% | 1.10 | 27° |
| 2 | 6% | 1.06 | 29° |
| 3 | 4% | 1.04 | 29° |
| 4 | 4% | 1.04 | 29° |
| 5 | 8% | 1.09 | 29° |
| 6 | 6% | 1.06 | 28° |
| 7 | 4% | 1.04 | 29° |
| 8 | 6% | 1.06 | 29° |
| 9 | 7% | 1.07 | 28° |
| 10 | 9% | 1.10 | 29° |
| 11 | 6% | 1.06 | 29° |
| 12 | 8% | 1.08 | 29° |
| 13 | 6% | 1.07 | 29° |
| 14 | 8% | 1.09 | 28° |
| 15 | 9% | 1.10 | 29° |
| 16 | 6% | 1.06 | 28° |
| 17 | 12% | 1.14 | 29° |
| 18 | 6% | 1.06 | 28° |
| 19 | 7% | 1.07 | 29° |
| 20 | 7% | 1.07 | 29° |
| 21 | 7% | 1.08 | 28° |
| 22 | 8% | 1.09 | 28° |
| 23 | 4% | 1.04 | 28° |
| 24 | 9% | 1.10 | 28° |
| 25 | 4% | 1.04 | 29° |
| 26 | 7% | 1.09 | 27° |
| 27 | 7% | 1.09 | 28° |
| 28 | 8% | 1.09 | 28° |
| 29 | 4% | 1.04 | 28° |
| 30 | 6% | 1.06 | 29° |
| 31 | 6% | 1.06 | 28° |
| 32 | 6% | 1.06 | 29° |
| 33 | 4% | 1.04 | 28° |
| 34 | 7% | 1.08 | 28° |
| 35 | 4% | 1.05 | 29° |
| 36 | 4% | 1.05 | 28° |
| 37 | 9% | 1.10 | 28° |
| 38 | 6% | 1.07 | 27° |
| 39 | 9% | 1.10 | 28° |
| 40 | 8% | 1.09 | 29° |
| 41 | 7% | 1.07 | 30° |
| 42 | 7% | 1.07 | 26° |
| 43 | 10% | 1.11 | 29° |
| 44 | 8% | 1.08 | 28° |
| 45 | 7% | 1.08 | 27° |
| 46 | 9% | 1.10 | 29° |
| 47 | 9% | 1.10 | 28° |
| 48 | 9% | 1.10 | 27° |
| 49 | 8% | 1.09 | 26° |
| 50 | 7% | 1.08 | 26° |
| 51 | 8% | 1.09 | 26° |
| 52 | 9% | 1.10 | 29° |
| 53 | 8% | 1.09 | 30° |
| 54 | 9% | 1.10 | 26° |
| 55 | 8% | 1.08 | 28° |
| 56 | 10% | 1.11 | 27° |
| 57 | 7% | 1.07 | 26° |
| 58 | 8% | 1.09 | 29° |
| 59 | 7% | 1.08 | 26° |

TABLE XIV-continued

| Example | Compressibility index | Hausner ratio | Angle of repose |
|---|---|---|---|
| 60 | 7% | 1.08 | 28° |
| 61 | 8% | 1.09 | 29° |
| 62 | 8% | 1.09 | 30° |
| 63 | 8% | 1.08 | 28° |
| 64 | 7% | 1.08 | 27° |
| 65 | 9% | 1.10 | 28° |
| 66 | 9% | 1.10 | 27° |
| 67 | 9% | 1.10 | 27° |
| 68 | 9% | 1.09 | 28° |
| 69 | 8% | 1.09 | 29° |
| 70 | 7% | 1.08 | 26° |
| 71 | 7% | 1.08 | 27° |
| 72 | 9% | 1.10 | 28° |

The results indicate that the formulations have optimal flow properties, which were maintained even after 6 months of storage at room temperature. The mean bulk density of said compositions is 0.68 g/ml and the tapped density is 0.74 g/ml.

The invention claimed is:

1. An orodispersible powder composition, comprising:
a) a pharmacologically effective amount of an active pharmaceutical ingredient or a pharmaceutically acceptable salt thereof,
b) a ternary combination consisting of sodium citrate, citric acid and sucralose, and
c) one or more further excipients,
wherein the content of sodium citrate is comprised between 55 wt % and 85 wt %; the content of citric acid is comprised between 5 wt % and 30 wt %; and the content of sucralose is comprised between 5 wt % and 25 wt % over the total weight of the ternary composition,
wherein the content of the ternary combination is at least 8 wt % of the total orodispersible powder composition, and
wherein enzymes, steroids, triptans and anti-histaminic compounds are excluded as active pharmaceutical ingredient.

2. The orodispersible powder composition according to claim 1, wherein the active pharmaceutical ingredient is selected from an agent for attention deficit hyperactivity disorder (ADHD) therapy, analgesic agent, anti-asthmatic agent, anti-bacterial agent, anti-dementia agent, anti-depressant agent, anti-diabetic agent, anti-emetic agent, anti-epileptic agent, anti-hypercholesterolemia agent, anti-hypertensive agent, anti-inflammatory agent, anti-psychotic agent, anti-retroviral agent, anti-thrombotic agent, anti-viral agent, anxiolytic agent, agent for erectile dysfunction therapy, gastrointestinal function conditioning agent, chemotherapeutic agent, anti-Parkinson's agent, agent for cystic fibrosis therapy, agent for benign prostatic hyperplasia, and mixtures thereof; preferably selected from an agent for attention deficit hyperactivity disorder (ADHD) therapy, analgesic agent, anti-asthmatic agent, anti-bacterial agent, anti-dementia agent, anti-depressant agent, anti-diabetic agent anti-emetic agent, anti-epileptic agent, anti-hypercholesterolemia agent, anti-hypertensive agent, anti-inflammatory agent, anti-psychotic agent, anti-retroviral agent, anti-thrombotic agent, anti-viral agent, anxiolytic agent, agent for erectile dysfunction therapy, gastrointestinal function conditioning agent, anti-Parkinson's agent, and mixtures thereof.

3. The orodispersible powder composition according to claim 2, wherein the active pharmaceutical ingredient is selected from atomoxetine and lisdexamphetamine as agents for attention deficit hyperactivity disorder (ADHD) therapy; tramadol as analgesic; montelukast as anti-asthmatic; amoxycillin as anti-bacterial; donepezil and memantine as anti-dementia agents; fluoxetine and mirtazapine as anti-depressant agents; dapagliflozin, metformin, sitagliptin, vildagliptin, and mixtures thereof as anti-diabetic agents; ondansetron as anti-emetic agent; pregabalin as anti-epileptic agent; atorvastatin, ezetimibe, simvastatin, and mixtures thereof as anti-hypercholesterolemia agents; amlodipine, olmesartan medoxomil, hydrochlorothiazide (HCTZ), valsartan, candesartan, indapamide, perindopril, sacubitril, and mixtures thereof as anti-hypertensive agents; etoricoxib as anti-inflammatory agent; carbidopa, levodopa, entacapone, and mixtures thereof as anti-Parkinson's agents; aripiprazol and olanzapine as anti-psychotic agents; abacavir, lamivudine, dolutegravir, cobicistat, darunavir, emtricitabine, tenofovir alafenamide, tenofovir disoproxil, elvitegravir, efavirenz, rilpivirine, and mixtures thereof as anti-retroviral agents; clopidogrel and rivaroxaban as anti-thrombotic agents; acyclovir, elbasvir, grazoprevir, glecaprevir, pibrentasvir, ledipasvir, sofosbuvir, velpatasvir, voxilaprevir, and mixtures thereof as anti-viral agents; alprazolam as anxiolytic agent; dutasteride, tamsulosin, and mixtures thereof as agents for benign prostatic hyperplasia; ivacaftor, lumacaftor, and mixtures thereof as agents for cystic fibrosis therapy; tadalafil as agent for erectile dysfunction therapy; and butylscopolamine, domperidone and loperamide as gastrointestinal function conditioning agents.

4. The orodispersible powder composition according to claim 3, wherein the active pharmaceutical ingredient is selected from atomoxetine, lisdexamphetamine, tramadol, montelukast, amoxycillin, donepezil, memantine, fluoxetine, mirtazapine, dapagliflozin, metformin, sitagliptin, vildagliptin, ondansetron, pregabalin, atorvastatin, ezetimibe, simvastatin, amlodipine, olmesartan medoxomil, hydrochlorothiazide, valsartan, candesartan, indapamide, perindopril, sacubitril, etoricoxib, carbidopa, levodopa, entacapone, aripiprazol, olanzapine, abacavir, lamivudine, dolutegravir, cobicistat, darunavir, emtricitabine, tenofovir alafenamide, tenofovir disoproxil, elvitegravir, efavirenz, rilpivirine, clopidogrel, rivaroxaban, acyclovir, elbasvir, grazoprevir, glecaprevir, pibrentasvir, ledipasvir, sofosbuvir, velpatasvir, voxilaprevir, alprazolam, dutasteride, tamsulosin, ivacaftor, lumacaftor, tadalafil, butylscopolamine, domperidone, loperamide, and mixtures thereof.

5. The orodispersible powder composition according to claim 4, wherein the active pharmaceutical ingredient is a mixture selected from dapagliflozine/metformin, metformin/sitagliptin, metformin/vildagliptin, atorvastatin/ezetimibe, simvastatin/ezetimibe, amlodipine/olmesartan medoxomil, amlodipine/olmesartan medoxomil/hydrochlorothiazide, amlodipine/valsartan, amlodipine/valsartan/hydrochlorothiazide, candesartan/hydrochlorothiazide, indapamide/amlodipine/perindopril, olmesartan/amlodipine/hydrochlorothiazide, sacubitril/valsartan, carbidopa/levodopa/entacapone, abacavir/lamivudina/dolutegravir, cobicistat/darunavir, abacavir/lamivudine, cobicistat/darunavir/emtricitabine/tenofovir alafenamide, cobicistat/elvitegravir/emtricitabine/tenofovir alafenamide, emtricitabina/efavirenz/tenofovir disoproxil, emtricitabina/tenofovir alafenamide, emtricitabina/tenofovir disoproxil, tenofovir alafenamide/emtricitabine/rilpivirine, tenofovir disoproxil/emtricitabine/rilpivirine, elbasvir/grazoprevir, glecaprevir/pibrentasvir, ledipasvir/sofosbuvir, sofosbuvir/velpatasvir, sofosbuvir/velpatasvir/voxilaprevir, dutasteride/tamsulosin, and ivacaftor/lumacaftor.

6. The orodispersible powder composition according to claim 1, wherein the ternary composition comprises from 55 wt % to 85 wt % of sodium citrate, from 5 wt % to 30 wt % of citric acid and from 5 wt % to 25 wt % by weight of sucralose; wherein the amounts of sodium citrate, citric acid and sucralose in the ternary composition are combined to make 100%.

7. The orodispersible powder composition according to claim 1, wherein the content of the ternary composition is not more than 47 wt % over the total orodispersible powder composition.

8. The orodispersible powder composition according to claim 1, wherein one or more further excipients are selected from diluents, lubricants, glidants, flavouring agents, sweetening agents, acidulants, alkalizing agents, buffering agents, antioxidants and mixtures thereof.

9. The orodispersible powder composition according to claim 8, wherein the diluent is selected from mannitol, sorbitol, xylitol, isomalt, erythritol, cellulose powdered, microcrystalline cellulose, silified microcrystalline cellulose, starch, calcium phosphate, calcium lactate, calcium carbonate, magnesium carbonate, magnesium oxide and mixtures thereof.

10. The orodispersible powder composition according to claim 8, wherein the lubricant is selected from the group consisting of: talc, sodium benzoate, sodium stearyl fumarate, sodium lauryl sulfate, calcium stearate, magnesium stearate, zinc stearate, glyceryl behenate, stearic acid, glyceryl monostearate, poloxamer, polyethylene glycol and mixtures thereof.

11. The orodispersible powder composition according to claim 8, wherein the glidant is selected from the group consisting of: colloidal silicon dioxide, calcium phosphate tribasic, hydrophobic colloidal silica, magnesium silicate, magnesium trisilicate, silicon dioxide, talc and mixtures thereof.

12. The orodispersible powder composition according to claim 8, wherein the flavouring agent is selected from orange, banana, strawberry, cherry, wild cherry, lemon, cardamom, anise, peppermint, menthol, vanillin and ethyl vanillin and mixtures thereof.

13. A stick pack comprising the orodispersible powder composition according to claim 1.

14. A tablet comprising the orodispersible powder composition according to claim 1.

\* \* \* \* \*